United States Patent
de la Torre et al.

(10) Patent No.: US 7,341,558 B2
(45) Date of Patent: Mar. 11, 2008

(54) PERICARDIAL RETRACTOR

(75) Inventors: Ralph de la Torre, Swampscott, MA (US); William E. Cohn, Chestnut Hill, MA (US); Jose Luis Francese, Miami Springs, FL (US); Matthew A. Palmer, Miami, FL (US)

(73) Assignee: Medcanica, LLC, Miami, FL (US)

( * ) Notice: Subject to any disclaimer, the term of this patent is extended or adjusted under 35 U.S.C. 154(b) by 0 days.

(21) Appl. No.: 10/666,707

(22) Filed: Sep. 19, 2003

(65) Prior Publication Data

US 2005/0065409 A1 Mar. 24, 2005

(51) Int. Cl.
*A61B 1/32* (2006.01)
(52) U.S. Cl. ...................................... 600/204
(58) Field of Classification Search ................ 600/201, 600/204, 210, 216, 205, 208, 214, 219; 606/213, 606/232
See application file for complete search history.

(56) References Cited

U.S. PATENT DOCUMENTS

| | | | | |
|---|---|---|---|---|
| 5,021,059 A * | 6/1991 | Kensey et al. | ............... | 606/213 |
| 5,041,129 A | 8/1991 | Hayhurst et al. | | |
| 5,100,417 A * | 3/1992 | Cerier et al. | ................. | 606/139 |
| 5,123,914 A * | 6/1992 | Cope | ........................... | 606/232 |
| 5,211,650 A * | 5/1993 | Noda | ........................ | 606/139 |
| 5,217,486 A * | 6/1993 | Rice et al. | ................... | 606/232 |
| 5,289,817 A | 3/1994 | Williams et al. | | |
| 5,405,354 A * | 4/1995 | Sarrett | ........................ | 606/148 |
| 5,531,759 A | 7/1996 | Kensey et al. | | |
| 5,573,495 A | 11/1996 | Adler | | |
| 5,613,939 A | 3/1997 | Failla | | |
| 5,702,352 A | 12/1997 | Kimura et al. | | |
| 5,769,894 A * | 6/1998 | Ferragamo | .................. | 606/148 |
| 5,792,153 A * | 8/1998 | Swain et al. | ................ | 606/144 |
| 5,845,645 A * | 12/1998 | Bonutti | ...................... | 128/898 |
| 5,961,538 A * | 10/1999 | Pedlick et al. | .............. | 606/232 |
| 5,980,357 A * | 11/1999 | Newby | ....................... | 446/366 |
| 5,980,559 A * | 11/1999 | Bonutti | ...................... | 606/232 |
| 6,068,648 A * | 5/2000 | Cole et al. | ................... | 606/232 |
| 6,110,183 A * | 8/2000 | Cope | .......................... | 606/139 |
| 6,200,329 B1 * | 3/2001 | Fung et al. | ................. | 606/232 |
| 6,221,008 B1 | 4/2001 | Keckstein et al. | | |
| 6,315,789 B1 * | 11/2001 | Cragg | ........................ | 606/232 |
| 6,428,562 B2 * | 8/2002 | Bonutti | ...................... | 606/232 |
| 6,494,896 B1 * | 12/2002 | D'Alessio et al. | .......... | 606/213 |
| 6,592,609 B1 * | 7/2003 | Bonutti | ...................... | 606/232 |
| 6,635,073 B2 * | 10/2003 | Bonutti | ...................... | 606/232 |
| 6,652,563 B2 * | 11/2003 | Dreyfuss | .................... | 606/232 |

(Continued)

*Primary Examiner*—Eduardo C. Robert
*Assistant Examiner*—Michael B Priddy
(74) *Attorney, Agent, or Firm*—Gordon & Jacobson, PC (57) ABSTRACT

A surgical retractor includes a "swivel" having a string extending from one end and a string extending from the midpoint between the two ends. The swivel is delivered by pushing it out of a tube which is inserted through a small incision between the ribs of the patient. After the swivel is deployed, the tube is removed and the string which is attached to the center of the swivel is pulled to lift the pericardium. When the procedure is complete, the swivel is removed from the patient by pulling the string attached to the end of the swivel. According to one embodiment, the swivel is a cylinder with a blunt conical end. According to another embodiment, the swivel has a sharp end which is covered by a spring loaded collar.

19 Claims, 14 Drawing Sheets

U.S. PATENT DOCUMENTS 6,773,436 B2 * 8/2004 Donnelly et al. .............. 606/72
6,773,446 B1 * 8/2004 Dwyer et al. ................ 606/191
2004/0002735 A1 * 1/2004 Lizardi et al. .............. 606/232

* cited by examiner

Fig_21

PERICARDIAL RETRACTOR

BACKGROUND OF THE INVENTION

1. Field of the Invention

The invention relates to minimally invasive surgery. More particularly, the invention relates to a pericardial retractor for use in endoscopic heart surgery.

2. State of the Art

When performing surgery it is sometimes necessary to open and retract soft tissues that envelop or block access to the organs or structures to be operated on. For example, in endoscopic heart surgery it is necessary to suspend the pericardium in order to access the heart. However, tissue retraction is difficult in minimally invasive or endoscopic surgery because of the limits of space and the small number of entry sites.

Several devices exist for the retraction of tissue during endoscopic and laparoscopic surgery. These devices are designed to be delivered into the body through a small incision or through an introduction tube which passes through a small incision. Typically, the retraction devices include a deployable member which is attached to a string or cable. After the device is deployed on the distal side of soft tissue, the string is pulled out of the body, thereby lifting the tissue. (As used herein, the term "distal" means farther from the practitioner and the term "proximal" means closer to the practitioner.) When the tissue is sufficiently retracted, the device is held in place by clamping the string with a hemostat or other type of clamp.

U.S. Pat. No. 5,613,939 to Failla discloses several complex deployable devices. Some of them are difficult to deploy and most of them are difficult to remove when surgery is complete.

SUMMARY OF THE INVENTION

It is therefore an object of the invention to provide a surgical retractor.

It is also an object of the invention to provide a surgical retractor which is suitable for use in endoscopic surgery.

It is another object of the invention to provide an endoscopic surgical retractor which is suitable for lifting the pericardium during endoscopic heart surgery.

It is still another object of the invention to provide an endoscopic surgical retractor which is simple in its construction and its use.

It is yet another object of the invention to provide an endoscopic surgical retractor which is easily deployed and equally easy to remove from the body when surgery is complete.

In accord with these objects which will be discussed in detail below, the surgical retractor of the present invention includes a "swivel" having a string extending from one end and a string extending from the midpoint between the two ends. As used herein, the term "string" is meant to include any suitable string-like member, e.g. a cable, filament, suture, etc. Moreover, the two strings may actually be a single length of string which is looped through the swivel or which has opposite ends attached to the swivel. The swivel is delivered by pushing it out of a tube which, when used in endoscopic heart surgery, is inserted through a small incision between the ribs of the patient. When the swivel member is deployed, the tube is removed and the string which is attached to the center of the swivel is pulled to lift the pericardium. When the procedure is complete, the swivel is removed from the patient by pulling the string attached to the end of the swivel.

According to one embodiment, the swivel is a cylinder with a blunt conical end and an opposite keyed end. The keyed second end is engaged by the distal end of a pushrod which is movable through a delivery tube. The tube and/or pushrod may be hereinafter referred to as a "deployment tool". The proximal end of the delivery tube is coupled to a housing and the proximal end of the push rod is coupled to a push button in the housing. The push button has a locking ring which locks the pushrod in the deployed position when the push button is pushed. The strings attached to the swivel pass through the hollow pushrod and out of the housing. The strings are preferably different colors so that they can be distinguished one from the other. Alternatively, the strings may be labeled.

According to a second embodiment of the invention, the swivel has a sharp end which is covered by a spring loaded collar (safety shield). The swivel is coaxially mounted on the distal end of the delivery tube. The sharp end of the swivel is used to puncture the patient's chest and pericardium in order to introduce the device. Once introduced, the spring loaded collar slides over the sharp point so that it does not damage any tissues. A pushrod inside the delivery tube is used to deploy the swivel.

Additional objects and advantages of the invention will become apparent to those skilled in the art upon reference to the detailed description taken in conjunction with the provided figures.

DETAILED DESCRIPTION OF THE PREFERRED EMBODIMENTS

Referring now to FIGS. 1-12, a first embodiment of a surgical retractor 10 includes a hollow tube 12 having a proximal end 14 and a distal end 16. A hollow pushrod 18 extends through the hollow tube 12. The proximal end 14 of the tube 12 is coupled to a housing 20 which contains a push-button 22 which is coupled to the proximal end of the pushrod 18.

A bullet shaped "swivel" 24 is removably mounted in the distal end 16 of the tube 12. Two strings 26, 28 extend from the swivel 24 through the hollow tube 12 (preferably through the hollow pushrod 18) and exit through one or more holes 30 in the push-button 22. As used herein, the term "string" can mean cable or suture or filament or wire or other similar structure.

Figure 9:
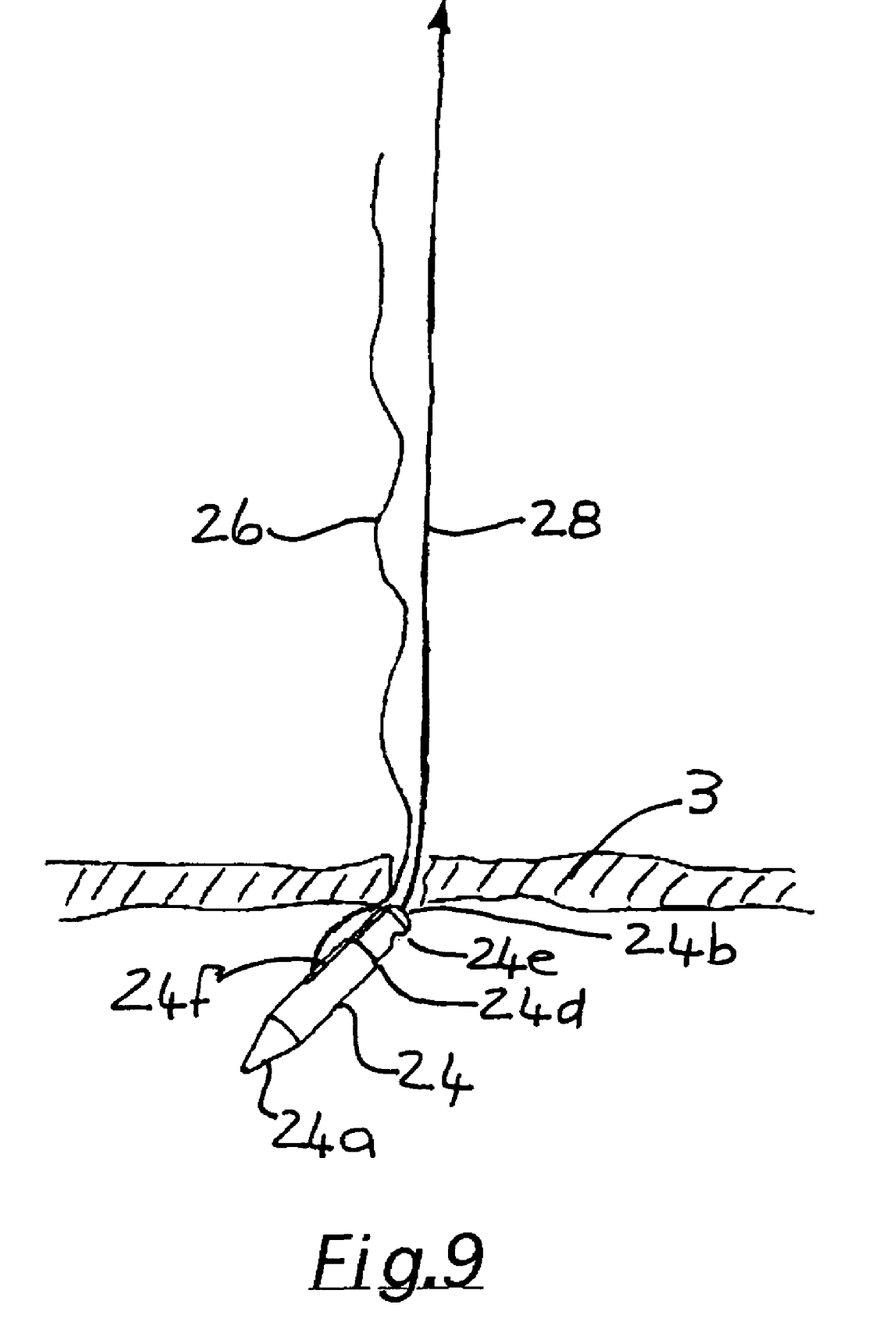
FIG. 9 is a broken side elevation view illustrating removal of the swivel after surgery.
Figure 11:
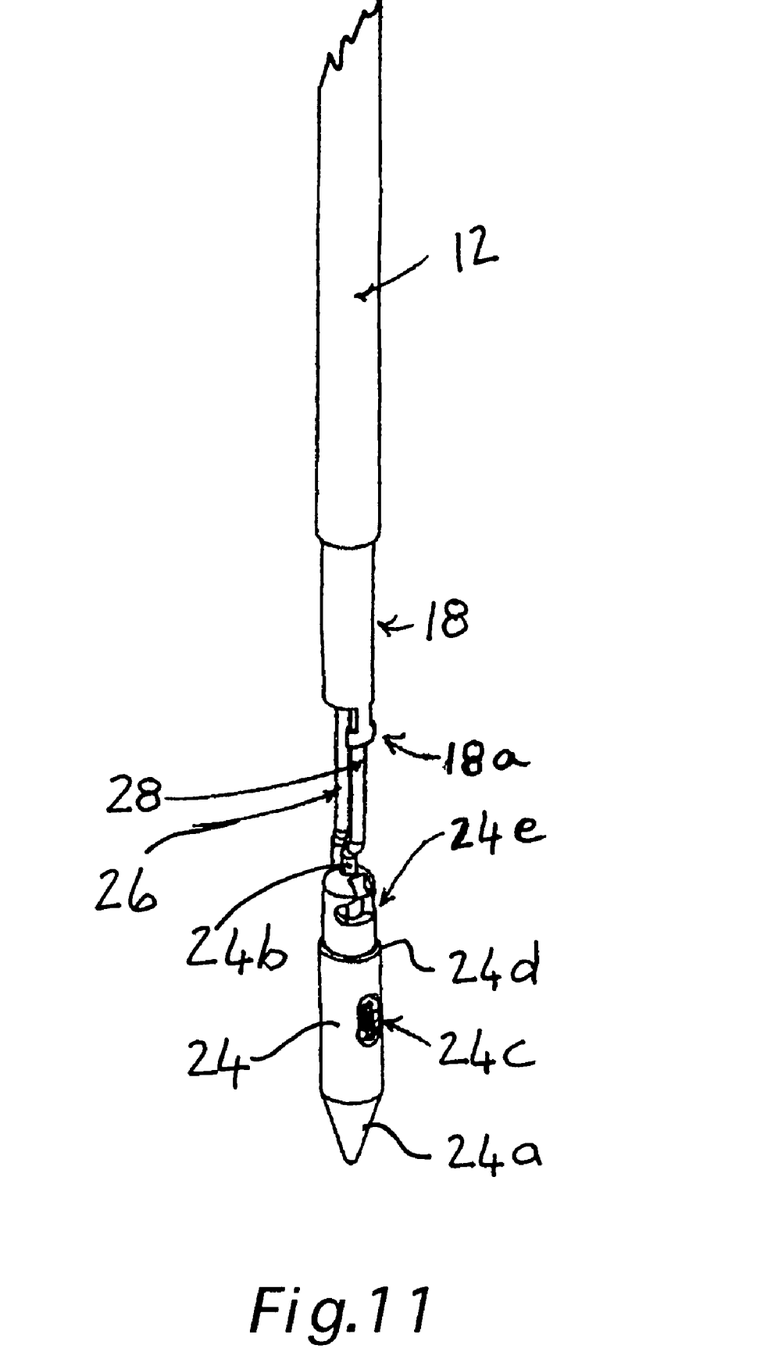
FIG. 11 is a broken perspective view of the distal end of the retractor with the swivel detached from the pushrod.

As seen best in FIGS. 9 and 11, one of the strings 26 extends from substantially the midpoint along the length of the swivel 24 and the other string 28 extends from the proximal end of the swivel 24. According to this embodiment, the swivel 24 has a blunt conical end 24a, an axial bore 24b, a radial bore 24c, a shoulder 24d, a T-shaped keyway 24e, and a surface groove 24f which extends from the bore 24c to the proximal end of the swivel 24. As seen best in FIG. 11, the strings 26, 28 are knotted together in the radial bore 24c. If the strings 26, 28 are a single length of string, a knot or similar structure is provided at 24c to prevent the string from detaching from the swivel.

As seen best in FIG. 11, the distal end of the pushrod 18 is provided with a T-shaped key 18a. This key is adapted to engage the keyway 24e in the proximal end of the swivel 24 prior to deployment of the swivel. This coupling is suggested in FIGS. 4 and 6. When the pushrod and swivel are coupled in this way, the proximal end of the swivel 24 up to the shoulder 24d is received by the distal end of the tube 12.

Figure 10:
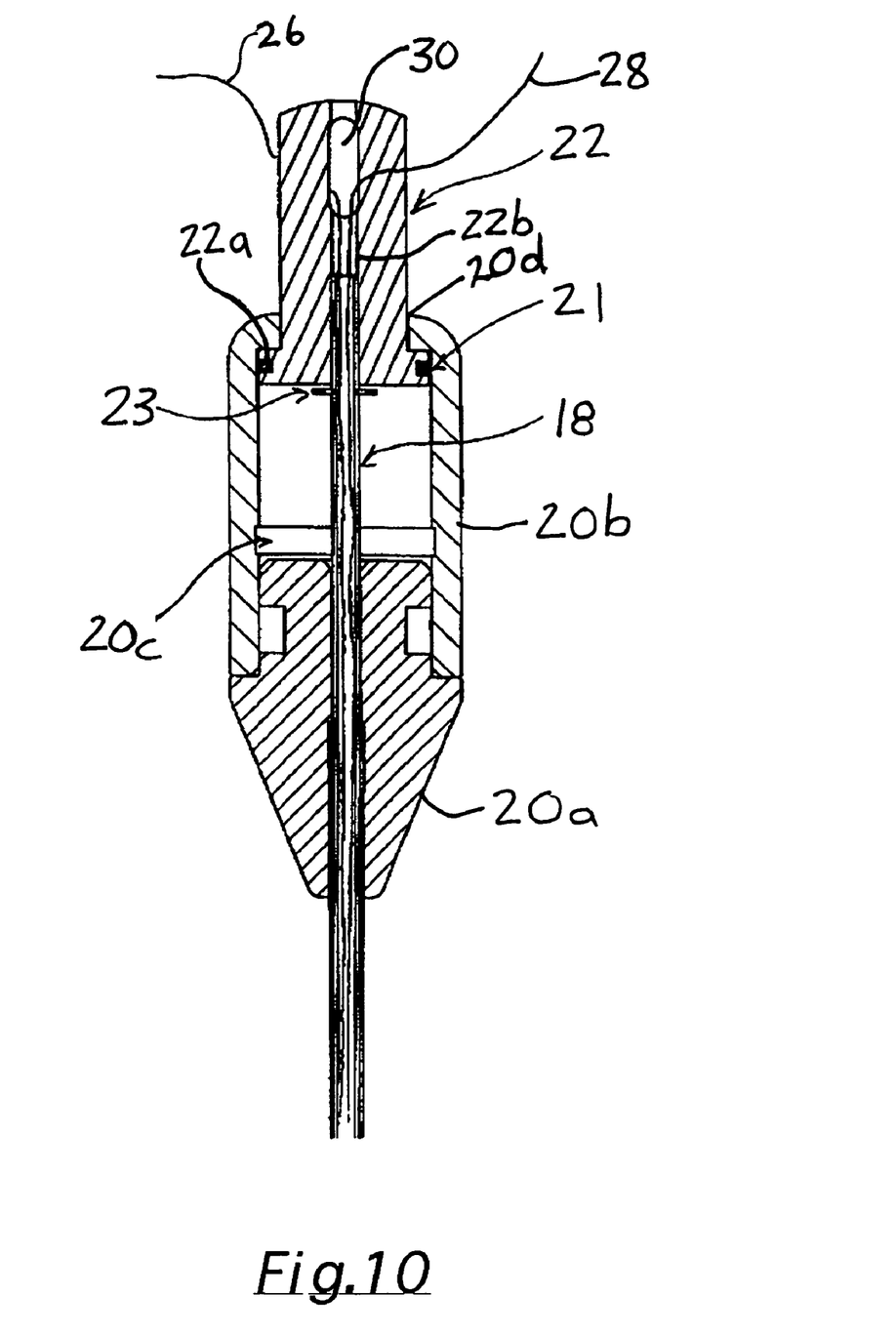
FIG. 10 is a broken longitudinal sectional view of the handle portion of the retractor.
Figure 12:
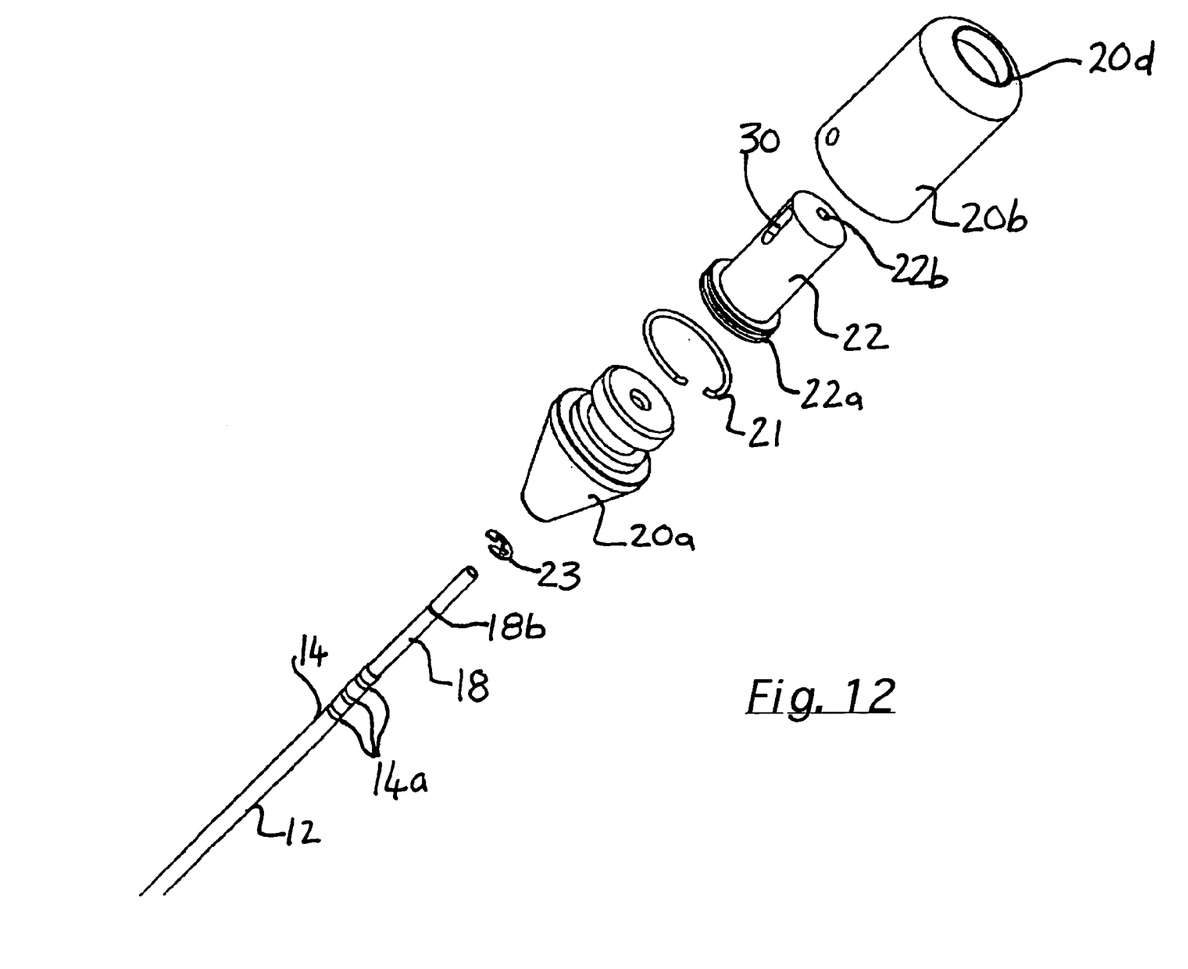
FIG. 12 is an exploded perspective view of the proximal handle portion of the retractor.

Turning now to FIGS. 10 and 12, the housing 20 has two parts: a distal ferrule 20a and a proximal cover 20b. The distal ferrule 20a is force fit onto annular ridges 14a at the proximal end 14 of the hollow tube 12 and the cover 20b is force fit or sonically welded to the ferrule 20a. The proximal cover 20b includes an interior locking groove 20c and a proximal opening 20d. The push-button 22 has a T-shaped profile with an annular groove 22a at the wider distal end and a central bore 22b which extends from the distal end to the string hole(s) 30. A locking ring 21 is placed in the annular groove 22a. The proximal end of the pushrod 18 is provided with an annular groove 18b which receives a thrust washer 23.

As seen best in FIG. 10, the narrow proximal part of the push-button 22 extends out of the proximal opening 20d of the cover 20b and the locking ring 21 frictionally engages the interior wall of the cover 20b. The proximal end of the pushrod extends into the central bore 22b of the push-button 22 and is prevented from passing through the push-button by the thrust washer 23. From the foregoing, it will be appreciated that the push-button may be moved from the position shown in FIG. 10 downward until it reaches the top of the ferrule 20a which prevents further downward movement. When the push-button 22 is fully depressed, the locking ring 21 engages the locking groove 20c and prevents the button from moving proximally.

Figures 1, 2:
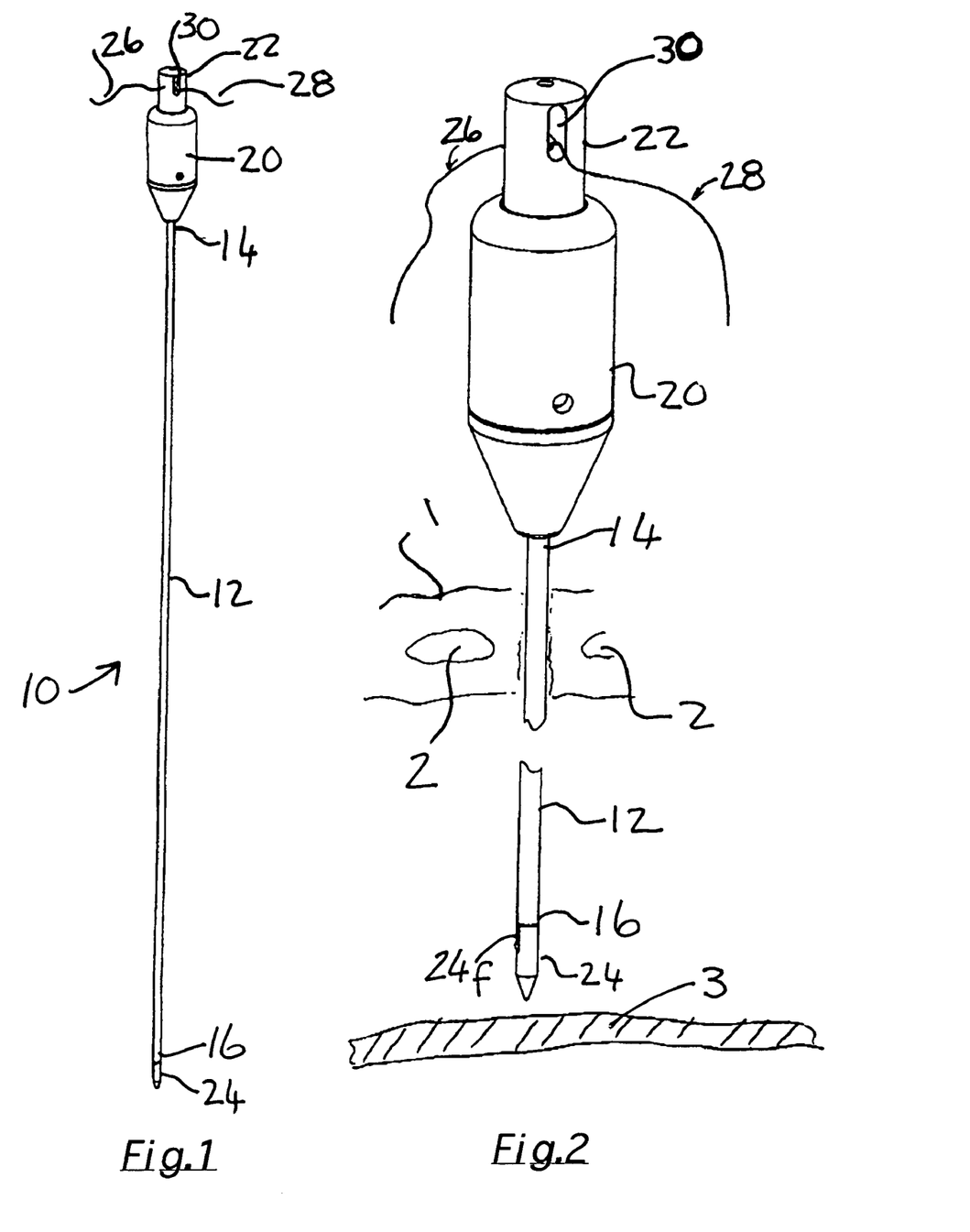
FIG. 1 is a perspective view of a first embodiment of a pericardial retractor according to the invention prior to insertion into the patient.
FIG. 2 is a broken perspective view of the retractor at initial insertion through the chest but prior to piercing the pericardium wall.

Turning now to FIGS. 1 and 2, the initial state of the retractor 10 has the push-button 22 in the proximalmost position with the swivel 24 coupled to the pushrod as previously described and the proximal end of the swivel embraced by (i.e. inside) the distal end 16 of the tube 12. It will be appreciated that in this state, the string 26 lies in the surface groove 24f of the swivel so that the string is not pressed between the swivel and the tube 12.

According to this embodiment, the conical tip 24a of the swivel 24 is not sharp enough to pierce the skin. Therefore, the first step in using the retractor is to make a small incision in the chest wall 1 (FIG. 2) between ribs 2. The retractor 10 is then inserted through the incision as shown in FIG. 2. The conical tip 24a of the swivel is sharp enough to puncture the pericardium 3 as shown in FIG. 4.

Figure 3:
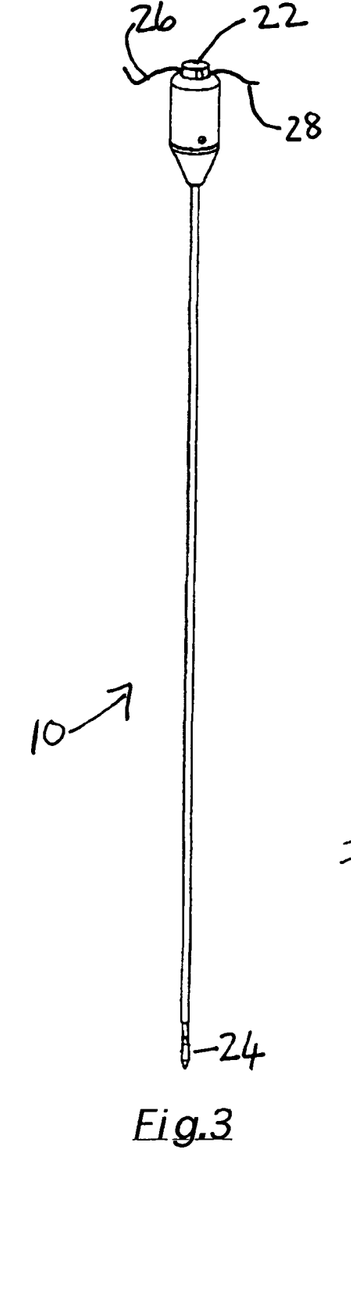
FIG. 3 is a perspective view of the retractor with the swivel partially deployed.
Figure 4:
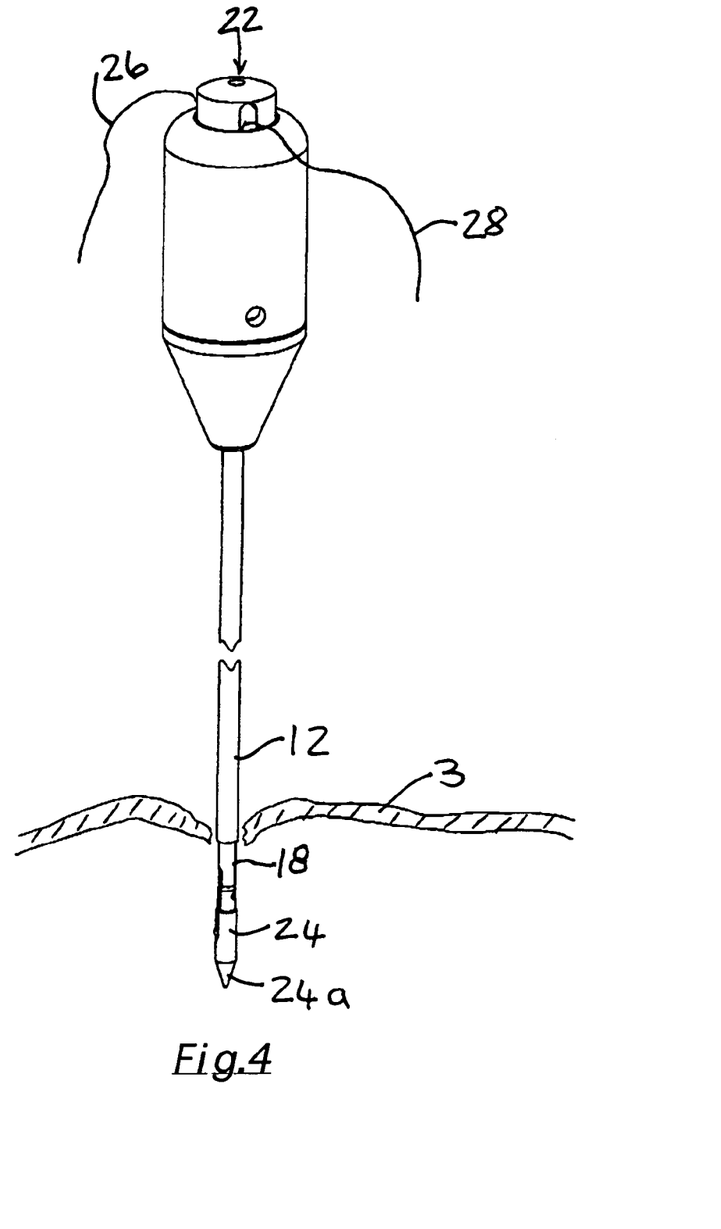
FIG. 4 is a broken perspective view of the retractor after piercing the pericardium with the swivel partially deployed.
Figure 5:
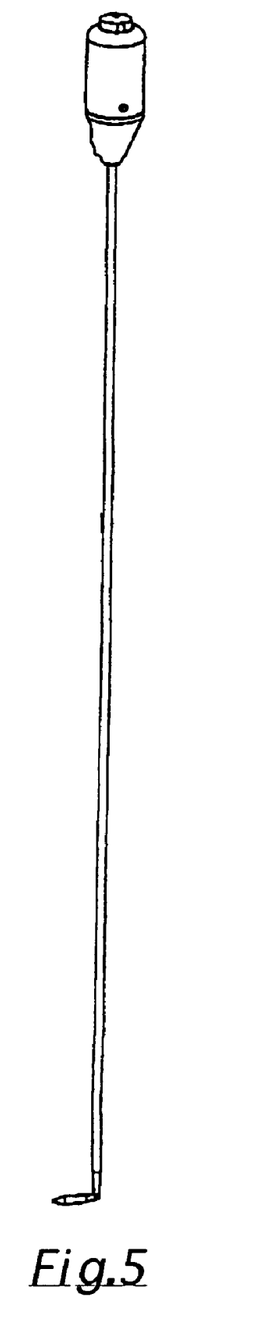
FIG. 5 is a perspective view of the retractor with the swivel fully deployed.
Figure 6:
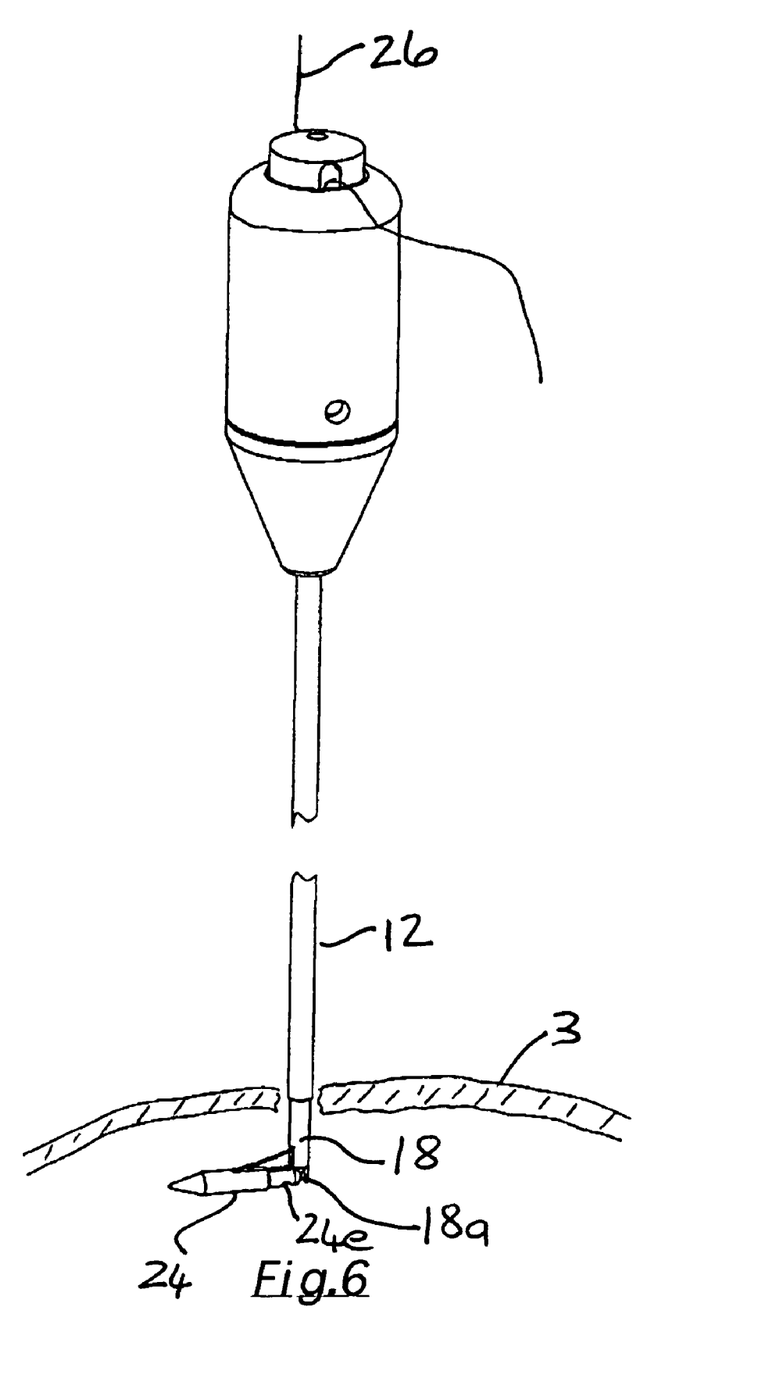
FIG. 6 is a broken perspective view of the retractor after piercing the pericardium with the swivel fully deployed.

After the pericardium is pierced, the push-button 22 is depressed as shown in FIGS. 3 and 4. This causes the pushrod 18 to move distally out of the tube 12 causing the swivel to move out of the tube as well. At this point, the key 18a of the push-rod 18 is still engaging the keyway 24e of the swivel 24. With the instrument configured in this manner, the string 26 which is attached to the middle of the swivel is pulled as shown in FIGS. 5 and 6. Because the string 26 extends on the opposite side of the swivel 24 from the T-shaped key 18, this causes the swivel 24 to "swivel" off the T-shaped key 18a at the distal end of the pushrod 18. When the string 26 has been pulled tight, the keyway 24e of the swivel 24 is no longer coupled to the key 18a of the pushrod 18.

Figure 7:
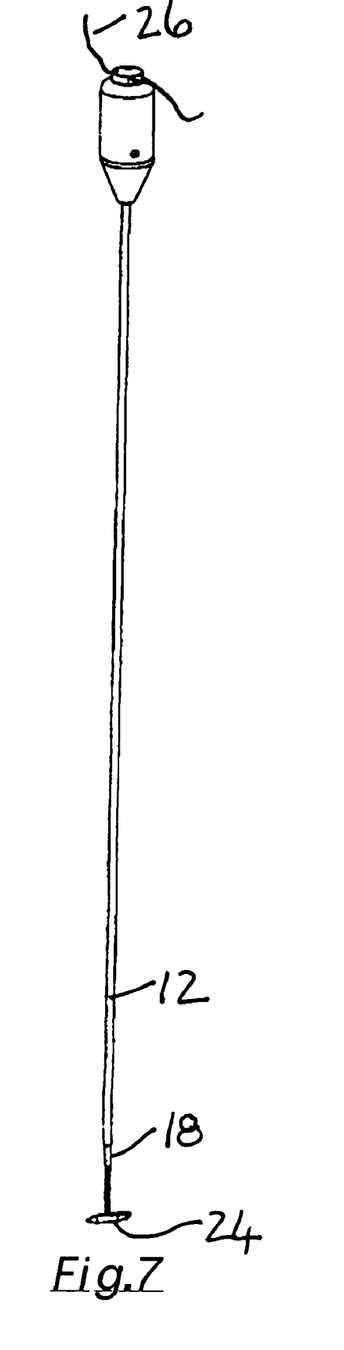
FIG. 7 is a perspective view of the retractor with the swivel fully deployed and released to perform retraction.
Figure 8:
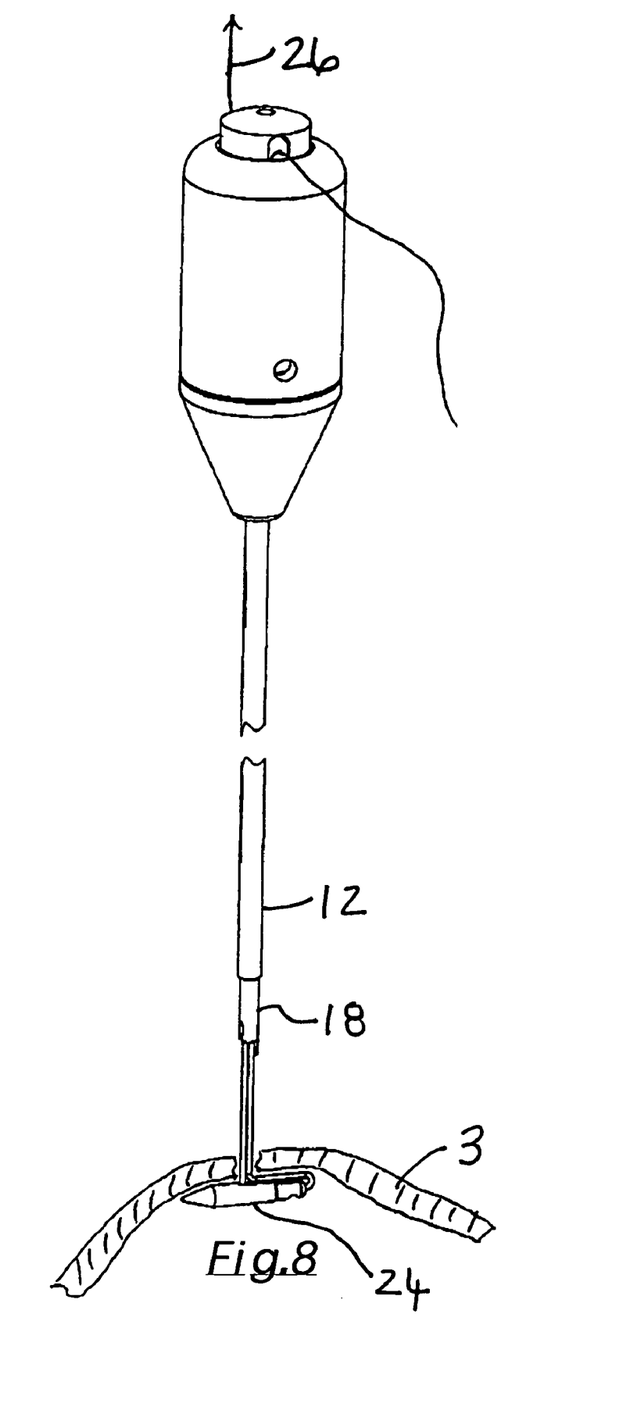
FIG. 8 is a broken perspective view of the retractor after piercing the pericardium with the swivel fully deployed and performing retraction.

Preferably, the tube 12 and pushrod 18 are then lifted out of the pericardium, away from the swivel 24 as shown in FIGS. 7 and 8. When this is done the swivel 24 remains inside the pericardium 3 as shown in FIG. 8. Pulling on the string 26 will retract the pericardium 3 because the swivel will remain substantially perpendicular to the string 26 and the axis of the incision in the pericardium 3. The pericardium may be held in the retracted position by clamping the string 26 with a hemostat or similar clamp.

When surgery is complete or when it is no longer necessary to retract the pericardium, the string 26 is released and the string 28 which is attached to the proximal end of the swivel 24 is pulled as shown in FIG. 9. This allows the swivel to be removed from the pericardium 3 and the chest 1 because the swivel will assume a direction coaxial to the string 28 and to the axes of the incisions in the pericardium and chest wall.

Particular features and advantages of the first embodiment include the following. The deployment, use and removal of the swivel is very simple and effective. The keyed connection between the pushrod and the swivel prevents the separation of the two until the push-button is pressed. It also prevents the axial rotation of the pushrod relative to the swivel or vice versa, which could cause the strings to become entangled. The locking feature of the push-button assures that the practitioner will always know whether the swivel has been deployed. Unlike some known endoscopic retractors, the retractor of the invention only -requires one entry site to deploy and remove. The point at the end of the swivel is sharp enough to pierce the pericardium (i.e. blunt dissection) but blunt enough to protect other tissues.

As mentioned above, it is preferable that the two strings 26, 28 be easily distinguishable from each other. This may be accomplished by color coding or by labeling.

A second embodiment of the invention is illustrated with no proximal actuator in FIGS. 13-21. From the following description, those skilled in the art will appreciate how the second embodiment can be used with the same proximal actuator 20, 22 shown in the previous Figures or used as shown.

Figures 13, 14:
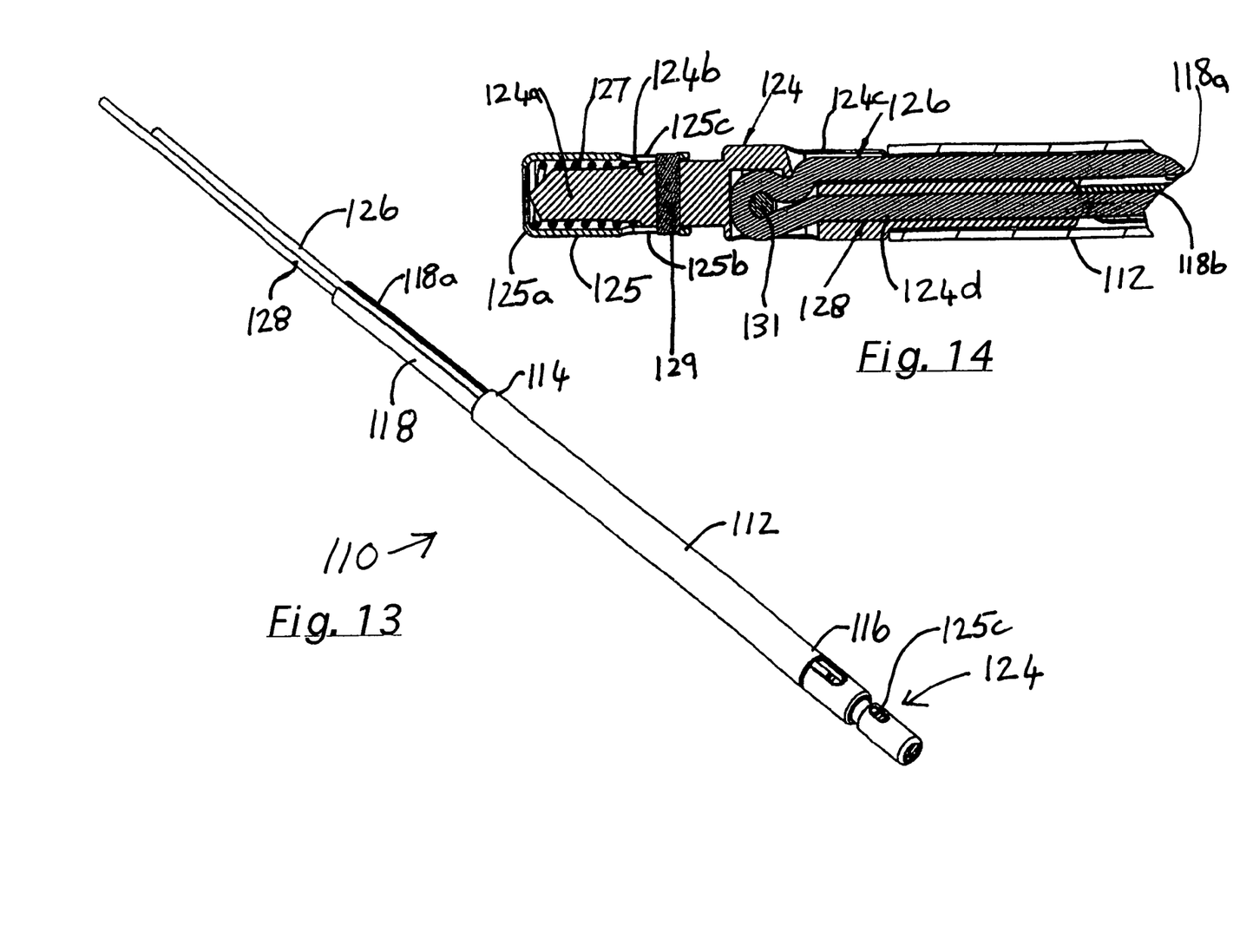
FIG. 13 is a broken perspective view of the distal portion of a second embodiment of the invention.
FIG. 14 is a broken sectional view of the distal end of the retractor of the second embodiment.

Referring now to FIGS. 13 and 14, the second embodiment 110 includes a hollow tube 112 having a proximal end 114 and a distal end 116. A pushrod 118 extends through the tube 112. In this embodiment, the pushrod 118 is not hollow but has a pair of surface grooves 118a, 118b. A swivel 124 is removably mounted on the distal end 116 of the tube 112. A pair of strings 126, 128 extend from the swivel 124 through the tube 112 along the grooves 118a, 118b in the pushrod 118. As seen in FIG. 14, the strings 126, 128 are actually a single string looped around a centrally located pin 131 in the swivel 124.

The distal portion of the swivel 124 has a sharp distal end 124a which is shaped like the point of a trocar (seen best in FIG. 21) and a shoulder 124b. The proximal end of the swivel has a surface groove 124c and a throughbore 124d which extend substantially half way to the distal end. A safety shield 125 having a distal shoulder 125a and a pair of longitudinal slots 125b, 125c is mounted over the distal end of the swivel with a spring 127 biased between the shoulders 124b and 125a. A diametrical pin 129 extends through the swivel proximal of the shoulder 124b and engages the slots 125b, 125c. Those skilled in the art will appreciate that the distal end of the swivel resembles a trocar used to make incisions during endoscopic and laparoscopic surgery. The proximal portion of the swivel is dimensioned to fit partially into the distal end 116 of the tube 112 and the distal portion is dimensioned to have approximately the same outer diameter as the tube 112. As seen best in FIG. 16, the distal end 118c of the pushrod 118 is rounded as is the proximal end 124e of the swivel 124 which abuts it.

From the foregoing, those skilled in the art will appreciate how the second embodiment of the invention is used. Starting with the instrument configured as shown in FIGS. 13 and 14, the distal end of the safety shield 125 is pressed against the chest wall between two ribs. The pressure causes the safety shield 125 to be pushed back against the spring 127 exposing the sharp end 124a of the swivel 124. Further pressure punctures the chest wall. When the shield 125 passes into the space between the chest wall and the pericardium, the spring 127 biases the shield 125 back to the safety position shown in FIGS. 13 and 14. Advancing the instrument further pierces the pericardium. The function of the shield is to prevent accidental damage to other tissues and to prevent ripping of the pericardium when the swivel is retracted.

Figure 15:
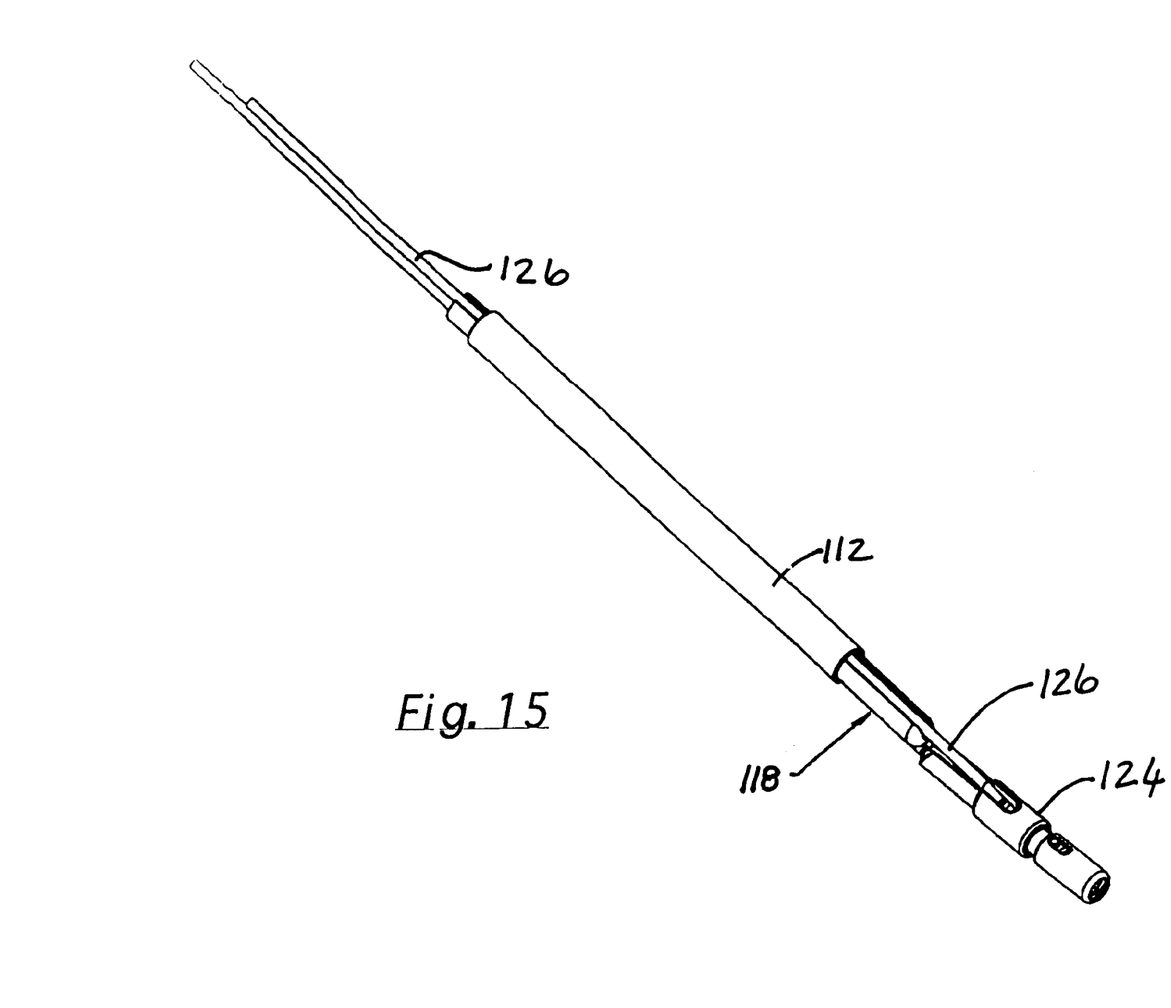
FIG. 15 is a view similar top FIG. 13 showing the swivel partially deployed.
Figure 16:
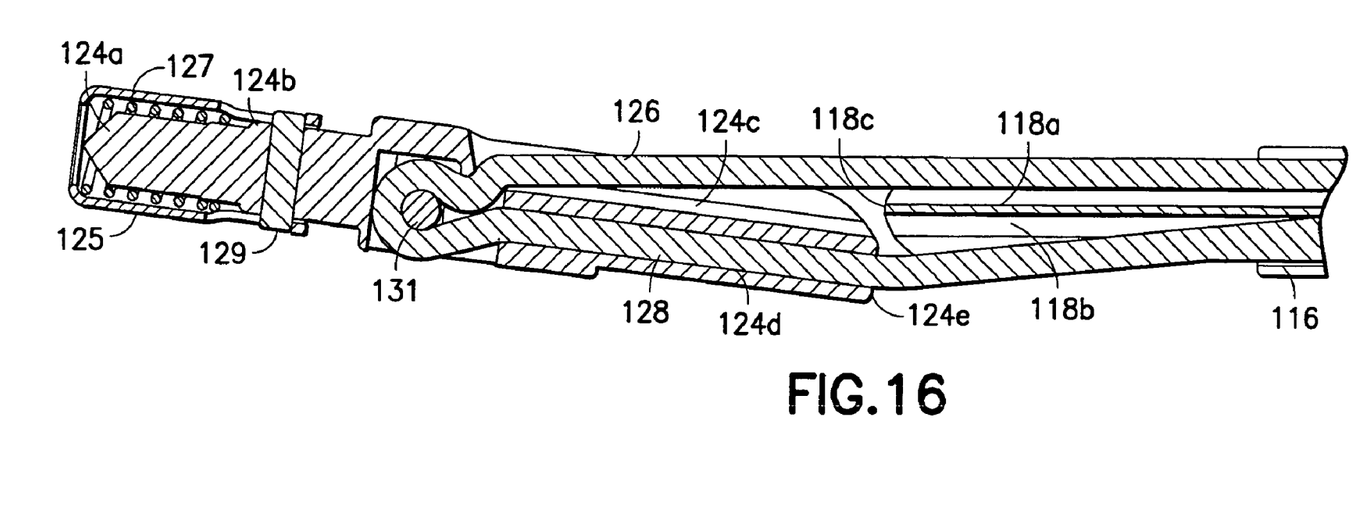
FIG. 16 is a view similar to FIG. 14 showing the swivel partially deployed.

After the pericardium is pierced, the pushrod 118 is advanced through the tube 112 as shown in FIGS. 15 and 16 releasing the swivel 124 from the distal end 116 of the tube 112. With the swivel released, the string 126 is pulled. This causes the swivel to rotate as shown in FIGS. 15 and 16. It will be appreciated that the curved surfaces 118c and 124e facilitate the rotation.

Figures 17, 18:
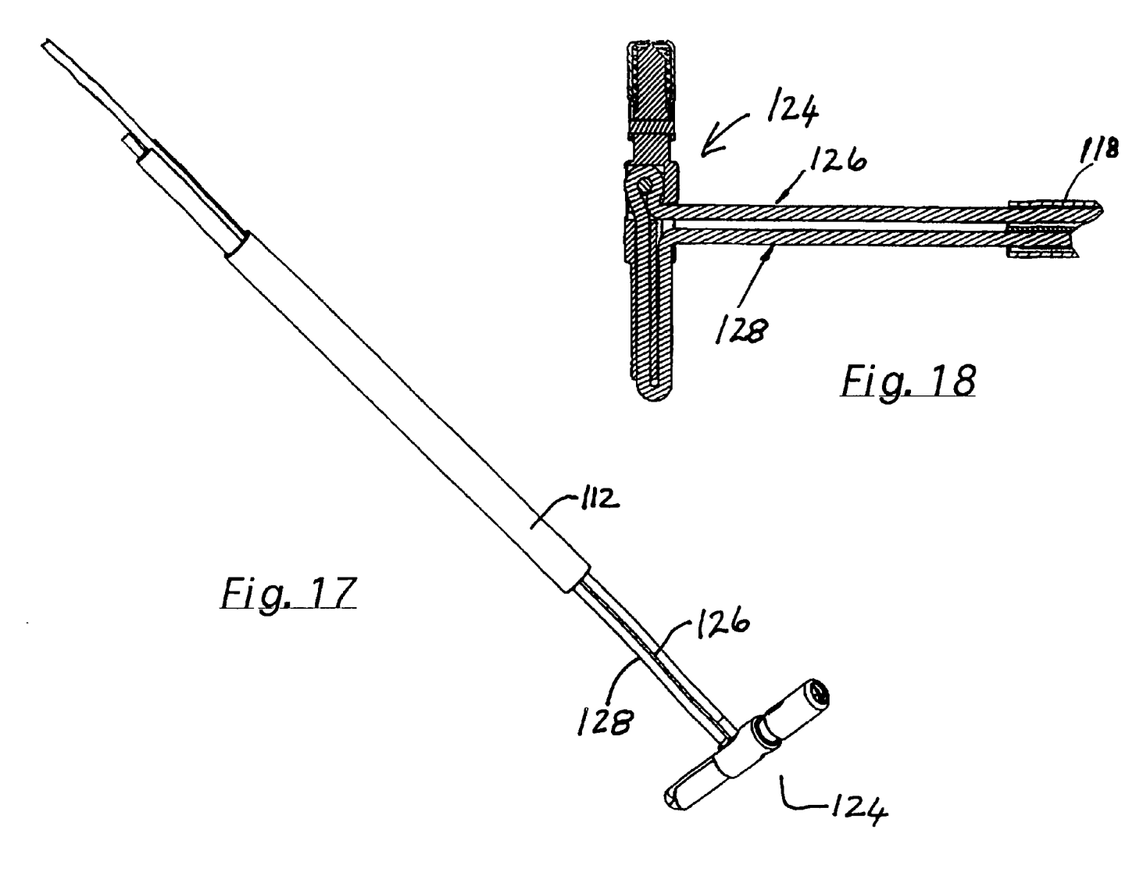
FIG. 17 is a view similar top FIG. 13 showing the swivel fully deployed.
FIG. 18 is a view similar to FIG. 14 showing the swivel fully deployed.

When the string 126 is pulled taut, the swivel 124 will assume a position approximately perpendicular to the string 126. The pushrod 118 may then be withdrawn as shown in FIGS. 17 and 18. Retraction of the pericardium is effected in the same way as described above with reference to the first embodiment.

Figure 19:
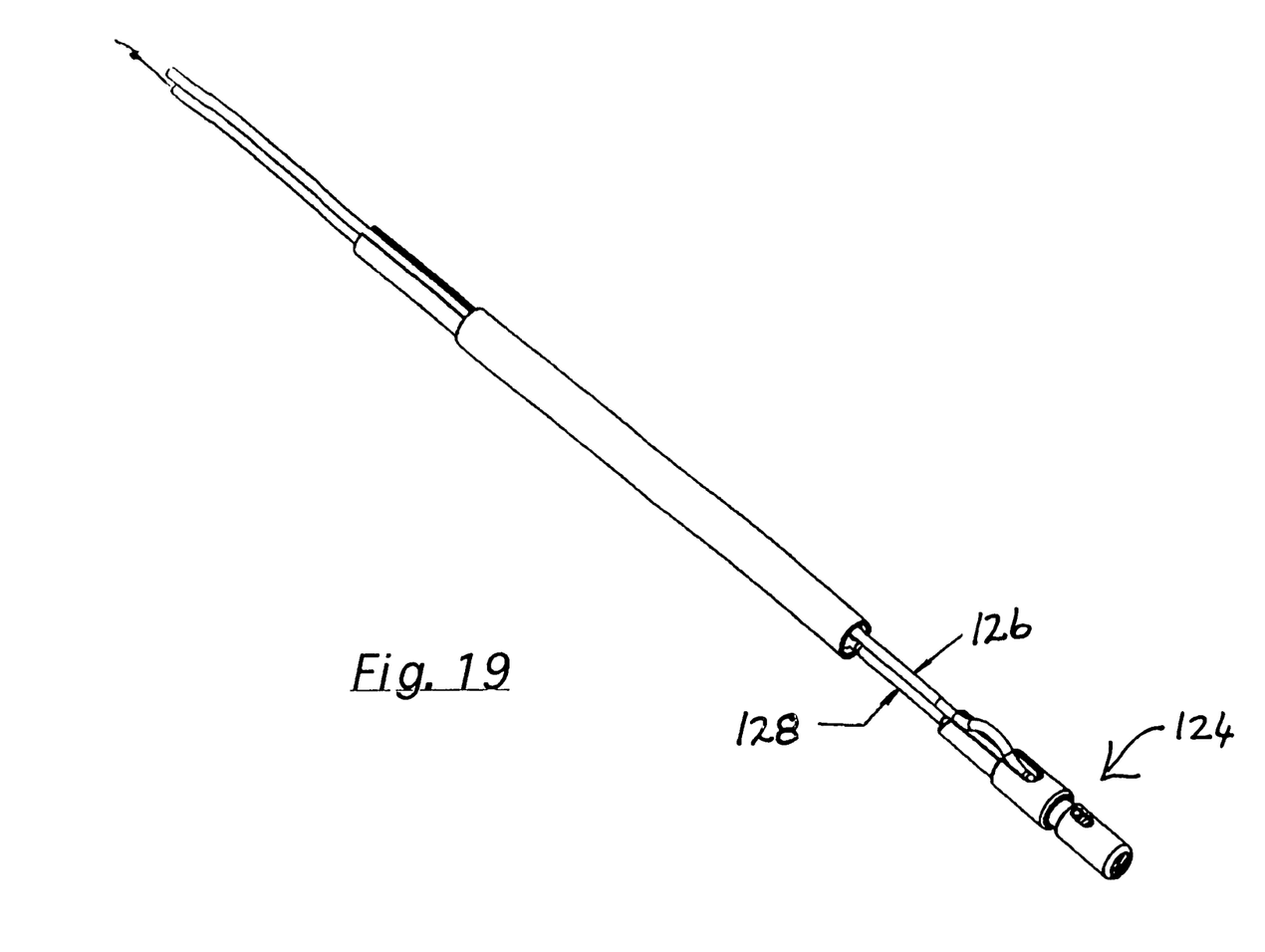
FIG. 19 is a view similar top FIG. 13 showing the swivel in position for removal from the surgical site.
Figure 20:
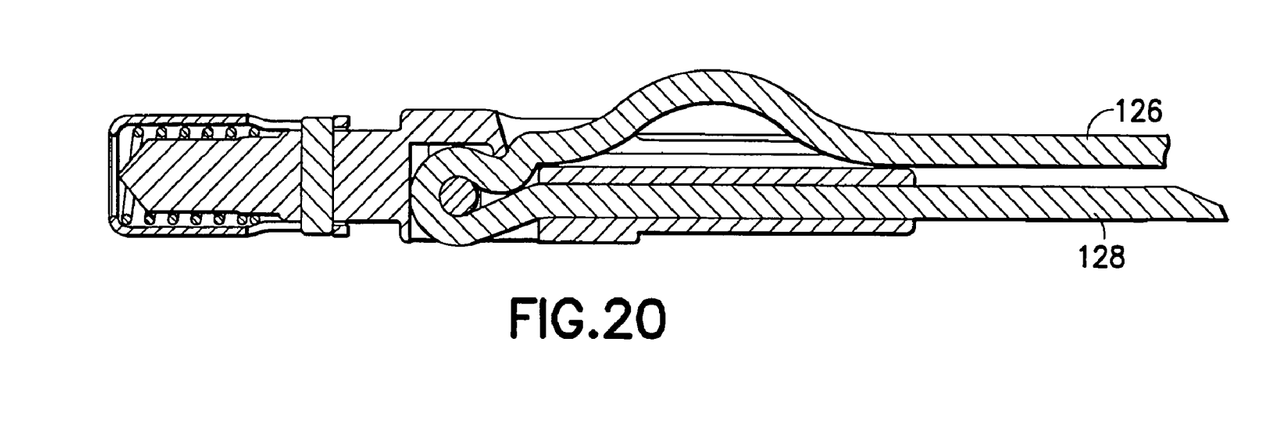
FIG. 20 is a view similar to FIG. 14 showing the swivel in position for removal from the surgical site.
Figure 21:
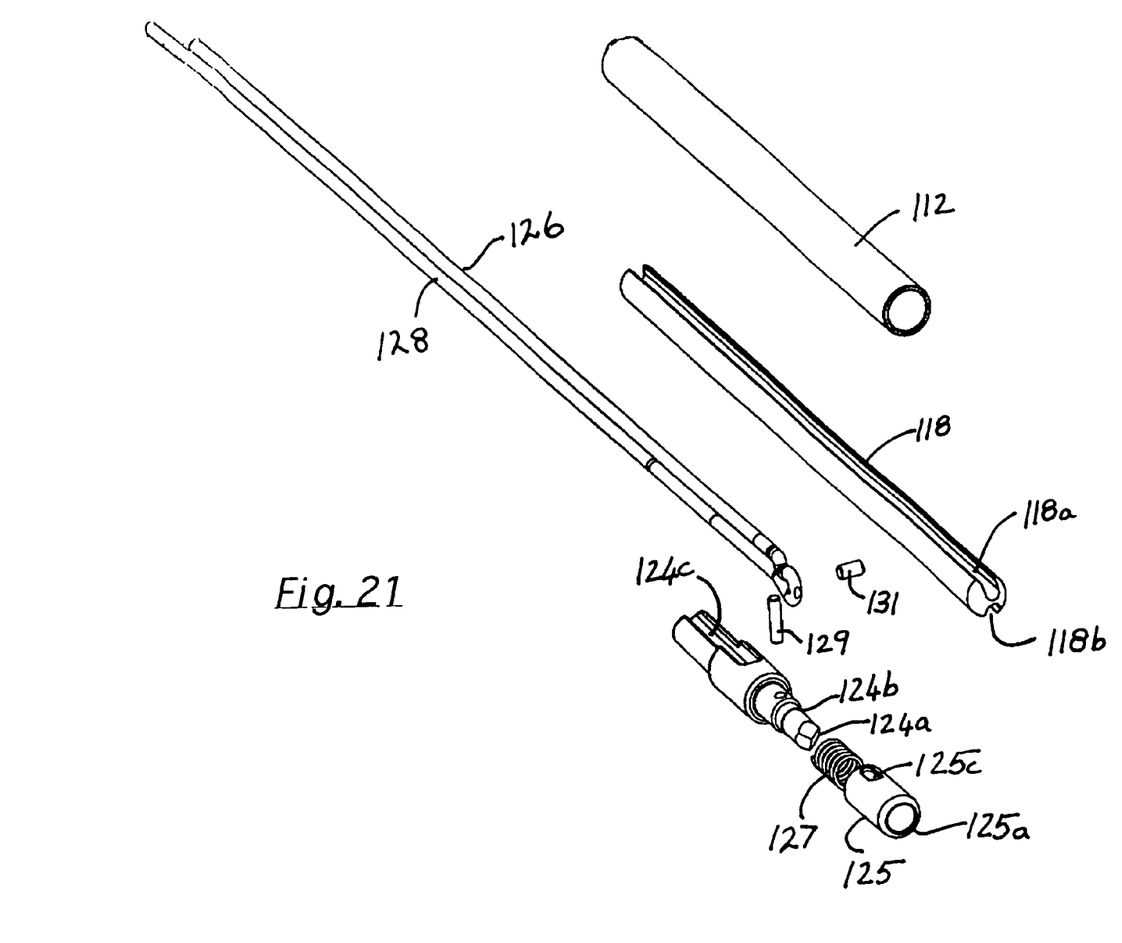
FIG. 21 is an exploded perspective view of the distal portion of the retractor.

When retraction is no longer needed, the swivel 124 is removed by pulling on string 128. This returns the swivel to a direction substantially collinear with the string 128 and coaxial to the axes of the incisions in the pericardium and the chest wall.

Particular features and advantages of the second embodiment include the following. The deployment, use and removal of the swivel is very simple and effective. When both strings are pulled, the surface grooves on the pushrod prevent the axial rotation of the swivel relative to the pushrod, which could cause the strings to become entangled. The retractor only requires one entry site to deploy and remove. The end of the swivel acts as a trocar and thus obviates the need for an incising tool.

There have been described and illustrated herein several embodiments of a pericardial retractor. While particular embodiments of the invention have been described, it is not intended that the invention be limited thereto, as it is intended that the invention be as broad in scope as the art will allow and that the specification be read likewise. Thus, while a particular proximal actuator has been disclosed, it will be appreciated that many of the advantages of the invention could be achieved without the proximal actuator or with a different proximal actuator. Also, while the tube, pushrod, and the swivel have all been illustrated and described as being substantially cylindrical, it will be recognized that other cross-sectional shapes could be used with similar results obtained. Moreover, while particular configurations have been disclosed in reference to the strings passing through the tube, it will be appreciated that many of the advantages of the invention could be obtained with one or both of the strings remaining outside the tube. In addition, while the invention was designed with the intention that it be used in endoscopic heart surgery, it may be used in other types of minimally invasive surgery. It will also be appreciated that an effective retractor could be made with the central string slightly off the midpoint of the swivel. It will therefore be appreciated by those skilled in the art that yet other modifications could be made to the provided invention without deviating from its spirit and scope as so claimed.

The invention claimed is:

1. A surgical retractor for use within a body cavity, comprising:
   a) an elongate swivel having a first end and a second end, said first end of said swivel having a non-circular keyway means for engaging a key on a deployment tool;
   b) a first length of string extending from said first end of said swivel;
   c) a second length of string extending from a point substantially midway between said first end and said second end, said second length of string having a free end which does not re-enter the swivel,
      said first and second lengths of string having sufficient length such that either may be pulled from outside the body cavity, such that
      pulling on said second length of string causes said swivel to swivel off the key on the deployment tool and be oriented substantially perpendicular to said second length of string, and
      pulling on said first length of string causes said swivel to be oriented substantially coaxial to said first length of string.

2. The surgical retractor according to claim 1, wherein:
said swivel is substantially cylindrical with said second end being substantially conical.

3. The surgical retractor according to claim 2, wherein:
said swivel has a reduced diameter portion adjacent to said first end.

4. The surgical retractor according to claim 1, wherein:
said swivel has a surface groove extending substantially from said first end to said point substantially midway between said first end and said second end, said surface groove having a depth sufficient to receive said second string.

5. The surgical retractor according to claim 1, wherein:
said swivel has an outer surface, an axial bore extending from said first end to said point substantially midway between said first end and said second end, and a radial bore extending from said axial bore to said surface at said point substantially midway between said first end and said second end.

6. The surgical retractor according to claim 5, wherein:
said first and second lengths of string are parts of a single length of string passing through said axial and radial bores.

7. The surgical retractor according to claim 5, wherein:
said first and second lengths of string are joined together where said axial bore intersects said radial bore.

8. The surgical retractor according to claim 1, wherein:
said first end of said swivel has a curved surface.

9. The surgical retractor according to claim 1, further comprising:
d) a hollow tube having a proximal end and a distal end, said first end of said swivel being removably mounted in said distal end of said tube; and
e) a pushrod having a proximal end and a distal end, said pushrod extending through said hollow tube with said distal end of said pushrod facing said first end of said swivel.

10. The surgical retractor according to claim 9, wherein:
said pushrod is hollow and said first and second lengths of string extend through said hollow pushrod and out of the proximal end of said hollow pushrod.

11. A surgical retractor according to claim 10, further comprising:
f) a housing coupled to said proximal end of said hollow tube; and
g) a push-button captured by said housing, wherein pushing said push-button into said housing engages said pushrod and moves it distally, pushing said swivel out of said distal end of said hollow tube.

12. The surgical retractor according to claim 11, wherein:
said push-button has an axial bore and a radial bore, said first and second lengths of string extending through said axial bore and said radial bore.

13. The surgical retractor according to claim 12, wherein:
said push-button and said housing have mutual locking means for locking said push-button in a depressed position.

14. The surgical retractor according to claim 13, wherein:
said mutual locking means includes a locking ring on said push-button and a locking groove in said housing.

15. The surgical retractor according to claim 11, wherein:
said pushrod is substantially solid having first and second longitudinal surface grooves,
said first and second lengths of string extending along said first and second longitudinal surface grooves and out of the proximal end of said hollow tube.

16. The surgical retractor according to claim 15, wherein:
said first end of said swivel has a curved surface and said distal end of said pushrod has a curved surface.

17. The surgical retractor according to claim 9, wherein:
said distal end of said pushrod has the key which engages said keyway means.

18. The surgical retractor according to claim 1, wherein:
said first length of string and said second length of string are visually distinguishable.

19. The surgical retractor according to claim 18, wherein:
said first length of string and said second length of string are different colors.

* * * * *